United States Patent [19]

Dumbraveanu et al.

[11] Patent Number: 5,716,342
[45] Date of Patent: Feb. 10, 1998

[54] NON-INVASIVE PRESSURE SENSOR

[75] Inventors: Gheorghe Dumbraveanu; Alex Urich, both of Mission Viejo; Michael Curtis, Lake Forest, all of Calif.

[73] Assignee: Circuit Tree Medical, Inc., Mission Viejo, Calif.

[21] Appl. No.: 540,501

[22] Filed: Oct. 10, 1995

[51] Int. Cl.$^6$ .................................................. A61M 1/00
[52] U.S. Cl. ................................................ 604/118; 73/715
[58] Field of Search ........................ 604/31, 67, DIG. 13, 604/118; 73/715–718, 719–731; 128/672–686; 222/105

[56] References Cited

U.S. PATENT DOCUMENTS

| | | |
|---|---|---|
| 3,301,063 | 1/1967 | Kisling . |
| 3,501,959 | 3/1970 | Womack . |
| 3,784,039 | 1/1974 | Marco . |
| 3,863,504 | 2/1975 | Borsanyi . |
| 4,226,124 | 10/1980 | Kersten . |
| 4,457,455 | 7/1984 | Meshberg . |
| 5,111,971 | 5/1992 | Winer . |
| 5,152,746 | 10/1992 | Atkinson et al. . |
| 5,454,784 | 10/1995 | Atkinson et al. . |

Primary Examiner—Mark Bockelman
Attorney, Agent, or Firm—Blakely Sokoloff Taylor & Zafman

[57] ABSTRACT

An adapter assembly for a pressure sensor. The adapter includes a sensor housing that has a first port and a second port that are both in fluid communication with an inner chamber of the housing. The assembly further includes a membrane housing that is pressed into the first port of the sensor housing and connected to a fluid line. Extending from the membrane housing is a membrane which separates the sensor housing inner chamber into a first subchamber and a second subchamber. The first subchamber is in fluid communication with the fluid line. The second subchamber is in fluid communication with a pressure transducer which is pressed into the second port of the sensor housing. Any variation of pressure within the fluid line will cause a change in the volume of the first subchamber. The change in the first subchamber volume will deflect the membrane and vary the volume of the second subchamber. In accordance with the ideal gas equation, the change of the second subchamber volume will vary the pressure of the second subchamber. The pressure transducer senses the change in the second subchamber pressure. The change in the second subchamber pressure corresponds to the variation in the line pressure. The membrane can be removed so that the pressure transducer can be reused even in contaminated environments.

6 Claims, 2 Drawing Sheets

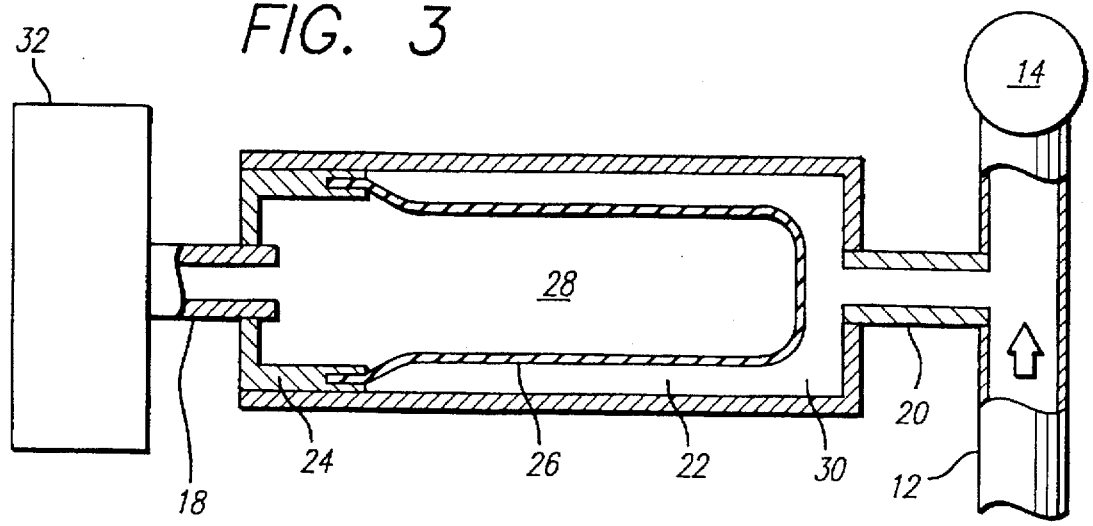
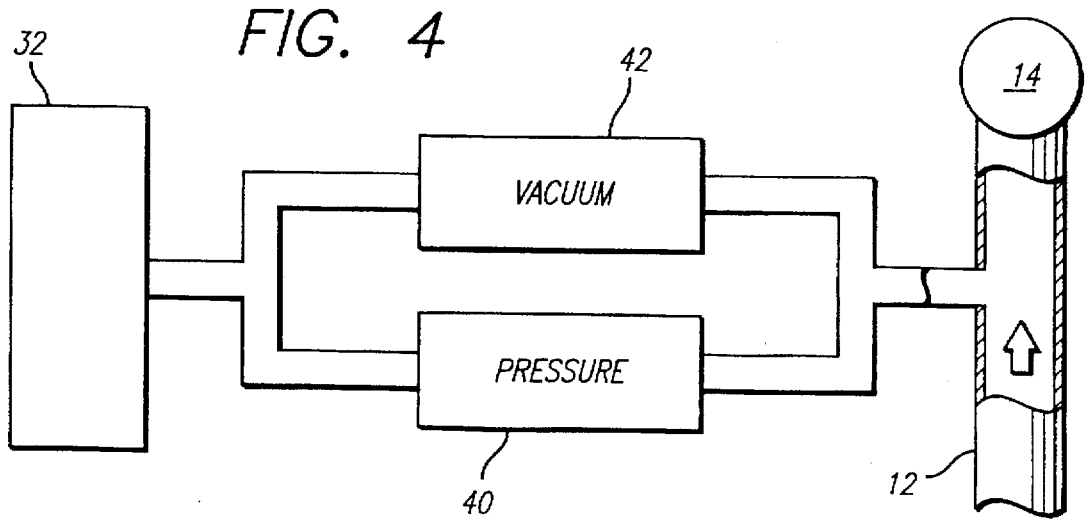

NON-INVASIVE PRESSURE SENSOR

BACKGROUND OF THE INVENTION

1. Field of the Invention

The present invention relates to a non-invasive pressure sensor for sensing the pressure of a fluid line.

2. Description of Related Art

In some systems it is desirable to sense the pressure of a fluid line. For example, interocular surgery is typically performed with an aspiration line that removes fluid and debris from the cornea of the patient. The aspiration line is connected to a pump which creates a vacuum that pulls the fluid from the eye. It is desirable to sense and display the vacuum pressure within the aspiration line to insure a safe and successful surgical procedure.

The fluid pressure is sensed by a pressure transducer that is connected to the aspiration line. The pressure transducer typically has a membrane that is in fluid communication with the aspiration fluid. Any variation in the fluid pressure creates a corresponding deflection of the transducer membrane. The deflection of the membrane is converted to an electrical signal which is provided to a display device.

The aspiration fluid may carry viruses, etc. from the patient that contaminate the transducer membrane. This contamination may be introduced to another patient thereby creating a health risk. For example, if the transducer is used for a subsequent procedure, the surgeon may dislodge an occlusion by pushing aspiration fluid back through the aspiration line. The back flow of aspiration fluid may introduce contaminants of the transducer membrane to the patient. Sterilizing the transducers is time consuming and not always reliable. Replacing the transducers is economically undesirable. It would be desirable to provide an adapter that allowed a pressure transducer to sense fluid pressure without creating contact between the transducer and the fluid.

SUMMARY OF THE INVENTION

The present invention is an adapter assembly for a pressure sensor. The adapter includes a sensor housing that has a first port and a second port that are both in fluid communication with an inner chamber of the housing. The assembly further includes a membrane housing that is pressed into the first port of the sensor housing and connected to a fluid line. Extending from the membrane housing is a membrane which separates the sensor housing inner chamber into a first subchamber and a second subchamber. The first subchamber is in fluid communication with the fluid line. The second subchamber is in fluid communication with a pressure transducer which is pressed into the second port of the sensor housing. Any variation of pressure within the fluid line will cause a change in the volume of the first subchamber. The change in the first subchamber volume will deflect the membrane and vary the volume of the second subchamber. In accordance with the ideal gas equation, the change of the second subchamber volume will vary the pressure of the second subchamber. The pressure transducer senses the change in the second subchamber pressure. The change in the second subchamber pressure corresponds to the variation in the line pressure. The membrane can be removed so that the pressure transducer can be reused even in contaminated environments.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 3 is a cross-sectional view showing an alternate embodiment of the adapter;

FIG. 4 is a schematic of a pressure transducer system with a pair of adapters.

DETAILED DESCRIPTION OF THE INVENTION

Figure 1:
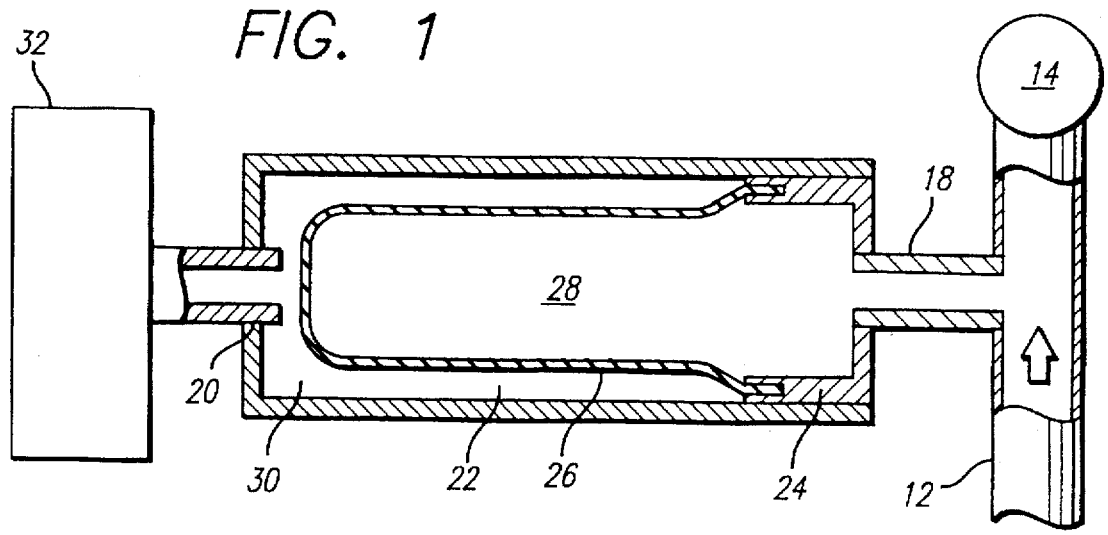
FIG. 1 is a cross-sectional view of a pressure transducer adapter of the present invention.

Referring to the drawings more particularly by reference numbers, FIG. 1 shows a pressure sensing system 10 of the present invention. The system 10 includes a fluid line 12. The fluid line 12 may be connected to a pump 14 that either increases or decreases the pressure within the line. By way of example, the fluid line 12 may be an aspiration line used to perform interocular surgical procedures. The pump 14 may create a vacuum that pulls fluids and debris from the surgical site. The surgical system may also have a supply line and a fluid source (not shown) which provide aspiration fluid to the surgical site, as is well known in the art. Although an aspiration line for a surgical procedure is described, it is to be understood that the pressure sensing system 10 of the present invention can be used to sense any fluid pressure.

The system 10 includes a sensor housing 16 that has a first port 18 and a second port 20. The ports 18 and 20 are in fluid communication with an inner chamber 22 of the housing 16. Pressed into the first port 18 is a membrane housing 24. Attached to the membrane housing 24 and extending into the inner chamber 22 is a membrane 26. The membrane 26 separates the inner chamber 22 into a first subchamber 28 and a second subchamber 30. The first subchamber 28 is in fluid communication with the fluid line 12. The second subchamber 30 is in fluid communication with a pressure transducer 32 that is connected to the second port 20. The membrane 26 is preferably constructed from a silicone rubber material with enough stiffness and structural memory to retain its shape when surrounded by air at atmospheric pressure.

The membrane housing 24 is preferably connected to the sensor housing 16 and fluid line 12 so that the membrane 26 can be removed from the inner chamber 22 and detached from the line 12. Likewise, the pressure transducer 32 is detachable from the sensor housing 24 to provide a modular sensor system 10. The membrane 26 is detachable so that the pressure transducer 32 can be used in multiple surgical procedures. The detachable membrane 26 prevents the pressure transducer 32 from being exposed to contaminants in the fluid line 12.

Although separate sensor 16 and membrane 24 housings are shown and described, it is to be understood that the membrane 26 may be located within a single housing. It being desirable to have a membrane 26 that divides a chamber with a fixed volume into a pair of subchambers which may vary in volume with a deflection of the membrane 26.

Figure 2:
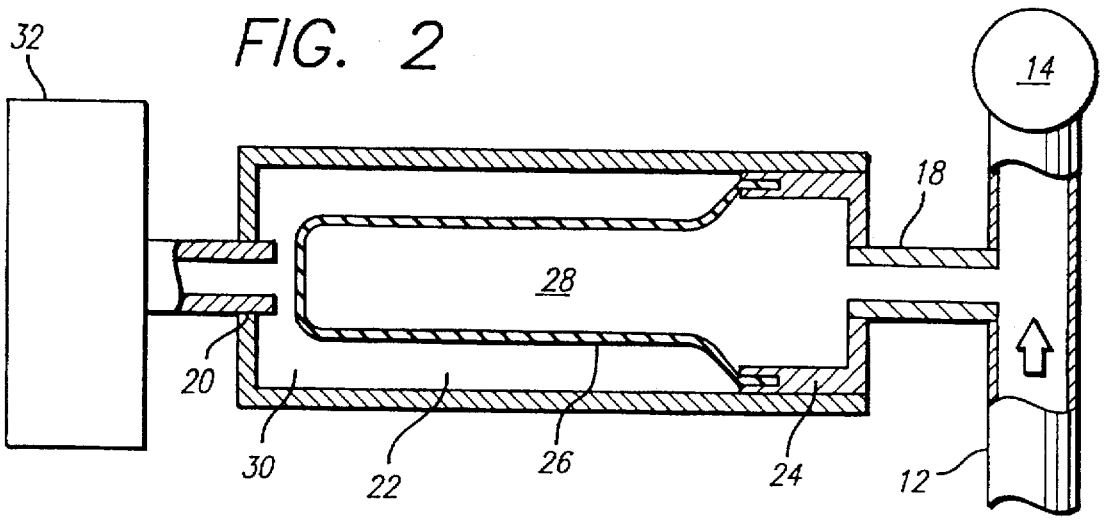
FIG. 2 is a cross-sectional view showing a membrane of the adapter being deflected.

As shown in FIG. 2, in operation, the membrane housing 24 is pressed into the sensor housing 16 to seal the second subchamber 30. The air trapped within the second subchamber 30 is typically at atmospheric pressure. The housings 16 and 24 may have corresponding lips and grooves (not shown) to facilitate the sealing of the second subchamber 30.

When the pressure within the fluid line 12 decreases, the pressure within the first subchamber 28 also decreases. When the pressure within the first subchamber 28 falls below atmospheric pressure the pressure within the second subchamber 30 will deflect the membrane 26 and reduce the volume of the first subchamber 28. The deflection of the membrane 26 and contraction of the first subchamber 28 will cause a corresponding expansion of the second subchamber 30. Assuming an isothermal process, under the ideal gas law any change in volume will produce a corresponding change in pressure. Therefore, the pressure of the second subchamber 30 will decrease as the volume of the subchamber 30 increases.

The volume will change until the second subchamber pressure is equal to the first subchamber pressure. The pressure transducer 32 senses the pressure of the second subchamber 30 which corresponds to the pressure of the first subchamber 28 and the fluid line 12. The adapter of the present invention thus allows a pressure transducer 32 to sense a fluid line 12 without exposing the transducer 32 to the fluid.

The amount of vacuum that can be sensed by the system is dependent upon the volume of the subchambers 28 and 30. The maximum level of vacuum is defined by the following equation:

$$\frac{V_1}{V_2} \equiv \frac{P_a}{P_a - P_{max}}$$

where;

$P_{max}$=maximum vacuum pressure measured by the sensor.
$P_a$=atmospheric pressure.
$V_1$=volume of the first subchamber.
$V_2$=volume of the second subchamber.

It is desirable to provide a second subchamber volume which is smaller than the first subchamber to maximize the amount of vacuum measured by the pressure sensor. Additionally, the smaller second subchamber volume reduces the fluid inertia and increases the response time of the system. The membrane 26 also functions as an accumulator which will absorb and dampen any pressure spikes in the fluid line 12.

FIG. 3 shows an alternate embodiment of a pressure system that is preferably used to sense positive pressures in the system. The housings 16 and 24 are reversed so that the pressure transducer 32 is in fluid communication with the first subchamber 28 and the fluid line 12 is in fluid communication with the second subchamber 30. The first subchamber 28 has a volume that is greater than the volume of the second subchamber 30 so that a maximum level of pressure can be measured by the system.

FIG. 4 is a schematic of a system which has a positive pressure adapter 40, shown in FIG. 3, and a vacuum pressure adapter 42, shown in FIG. 2, both coupled in parallel to a single pressure transducer 32 and the fluid line 12. The system can measure both positive and negative pressures with a single pressure transducer 32.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A pressure transducer assembly for a fluid line which has a line pressure, comprising:

a sensor housing that has a first port and a second port that are in fluid communication with an inner chamber of said sensor housing;

a membrane housing that is detachably connected to said first port and the fluid line;

a tubular shaped membrane that has a diameter and a longitudinal axis, said tubular shaped membrane has a first end coupled to said sensor housing and an opposite unsupported second end, said tubular shaped membrane having a length that extends from said first end to said second end, said length being greater than said diameter of said tubular shaped membrane, said membrane is attached to membrane housing and extends into said inner chamber, said membrane separates said inner chamber into a first subchamber that has a first volume and a second subchamber that has a second volume, said first subchamber is adapted to be in fluid communication with the fluid line, wherein a variation in the line pressure will vary said first volume of said first subchamber and deflect said membrane in a direction essentially perpendicular to the longitudinal axis of said membrane to vary the diameter of said membrane, wherein said membrane deflection varies said second volume of said second subchamber and varies a corresponding pressure within said second subchamber; and, a pressure transducer that is attached to said second port of and disposed outside of said sensor housing and is in fluid communication with said second subchamber, said pressure transducer senses the variation in said second subchamber pressure.

2. The assembly as recited in claim 1, wherein said first volume of said first subchamber is greater than said second volume of said second subchamber.

3. The assembly as recited in claim 2, wherein said membrane is constructed from a silicone rubber material.

4. A pressure transducer assembly for a fluid line which has a line pressure, comprising:

a sensor housing that has a first port and a second port that are in fluid communication with an inner chamber of said sensor housing, said first port being connected to the fluid line;

a membrane housing that is detachably connected to said second port;

a tubular shaped membrane that has a diameter and a longitudinal axis, said tubular shaped membrane has a first end coupled to said sensor housing and an opposite unsupported second end, said tubular shaped membrane having a length that extends from said first end to said second end, said length being greater than said diameter of said tubular shaped membrane, said membrane is attached to membrane housing and extends into said inner chamber, said membrane separates said inner chamber into a first subchamber that has a first volume and a second subchamber that has a second volume, said second subchamber is adapted to be in fluid communication with the fluid line, wherein a variation in the line pressure will vary said second volume of said second subchamber and deflect said membrane in a direction essentially perpendicular to the longitudinal axis of said membrane to vary the diameter of said membrane, wherein said membrane deflection varies said first volume of said first subchamber and varies a corresponding pressure within said first subchamber; and, a pressure transducer that is attached to and disposed outside of said membrane housing and is in fluid communication with said first subchamber, said pressure transducer senses the variation in said first subchamber pressure.

5. The assembly as recited in claim 4, wherein said first volume of said first subchamber is greater than said second volume of said second subchamber.

6. The assembly as recited in claim 5, wherein said membrane is constructed from a silicone rubber material.

* * * * *